United States Patent
Abdel-Monem

[11] 3,950,372
[45] Apr. 13, 1976

[54] 1:1 MANGANESE ALPHA AMINO ACID COMPLEXES

[75] Inventor: Mahmoud M. Abdel-Monem, South Minneapolis, Minn.

[73] Assignee: Zinpro Corporation, Chaska, Minn.

[22] Filed: July 3, 1974

[21] Appl. No.: 485,442

[52] U.S. Cl. ............................ 260/429 R; 260/999
[51] Int. Cl.² ........................................ C07F 13/00
[58] Field of Search .............................. 260/429 R

[56] References Cited
OTHER PUBLICATIONS
Chemical Abstracts, Vol. 78, 102647u (1973).
Chemical Abstracts, Vol. 71, 108570r (1969).
Chemical Abstracts, Vol. 61, 5012c (1964).
Chemical Abstracts, Vol. 77, 96420a (1972).
Kroll, J.A.C.S. Vol. 74, pp. 2034–2036 (1952).
Chemical Abstracts, Vol. 79, 118899j (1973).
Chemical Abstracts, Vol. 70, 33885r (1969).
Chemical Abstracts, Vol. 62, 1115d (1965).
Chemical Abstracts, Vol. 66, 119442y (1967).
Chemical Abstracts, Vol. 68, 117568m (1968).

*Primary Examiner*—Helen M. S. Sneed
*Attorney, Agent, or Firm*—Zarley, McKee, Thomte & Voorhees

[57] ABSTRACT

Novel salts are prepared wherein the cation of the salt comprises a 1:1 ratio complex of a complex ion formed between manganese and an alpha amino acid, and any suitable anion, either inorganic or organic but preferably a monovalent inorganic anion. The novel salts have the formula:

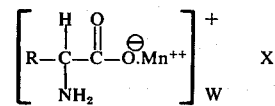

wherein X is an anion, W is an integer equal to the anionic charge of X, and R is an alpha position moiety of an essential amino acid. The preferred amino acids are methionine and glycine. These compounds are useful nutritional supplements, both for animals and humans in that they provide a readily available source of manganese ions necessary for dietary balance. In addition, these complexed salts also provide a readily available source for certain amino acids needed in a balanced diet, such as methionine.

5 Claims, No Drawings

1:1 MANGANESE ALPHA AMINO ACID COMPLEXES

BACKGROUND OF THE INVENTION

The importance of an adequate supply of manganese to the diet of both animals and humans has been reported in the literature. Adequate dietary intake of manganese for swine, cattle, and poultry has been shown for sometime to be of importance. For example, in both birds and mammals, manganese deficiency has been reported in the literature as characterized by bone abnormalities, defective growth, central nervous system manifestations, reproductive disfunction, and abnormalities in fat and lipid metabolism.

Thus, manganese is considered as essential in nutrition for several reasons. First, it is omnipresent in food stuff. Secondly, its concentration in mammalian tissues is steady, fairly characteristic of each organ, and not species-linked. Third, it shows numerous impressive biochemical functions in vitro. Fourth, when diets deficient in manganese are eaten, specific symptoms result. Fifth, when given to severely manganese deficient animals, the addition of manganese specifically and reproducively relieves a major part of their deficiency symptoms. Sixth, when given as a dietary supplement it prevents symptoms of deficiency from appearing.

While the importance of an adequate manganese level in the diet of both animals and humans has been shown and reported for sometime, maintenance of adequate manganese levels in the dietary intake has not necessarily been easy to achieve. Dietary supplementation with inorganic salts or manganese, such as manganese sulfate and manganese chloride, seems to be inadequate since it does not simulate the state of manganese in foods. Manganese in food is probably present in the form of mettalloorganic complexes. Furthermore, examination of the contents of the guts of a number of animals revealed that manganese was present in the form of metalloorganic complexes and not in the inorganic state. The enchancement of the absorption of a number of metal ions, including manganese, from the gastrointestinal tract of chicken in presence of unnatural complex forming agents, e.g. ethylene diamine tetracetic acid, has been previously established. These unnatural complex forming agents were found to have detrimental effects on the utilization of some metals including manganese since they form stable complexes with these metals which are readily excreted. It is therefore essential to choose ligands which will form complexes of intermediate stability with manganese to enhance the absorption of the metal from the gastrointestinal tract and would release the metal for utilization within the animal body. Amino acids are examples of these types of ligands. Naturally occurring amino acids form complexes with metals, including manganese, of intermediate stability and it has been postulated that amino acid metal complexed are involved in the reabsorption of metals in the kidneys. Dietary supplementation with manganese in the form of amino acid complex would enhance the absorption of the metal from the gastrointestinal tract and in the blood the complex would provide both the amino acid and manganese for utilization by the animal. These amino acid complexes are soluble in water and the solution is stable under conditions simulating the gastric and intestinal contents.

Accordingly, it is an object of this invention to provide novel manganese compounds wherein the manganese is in a form which can be readily absorbed after ingestion by animals and readily distributed and utilized in order to provide adequate manganese levels for proper health, weight gain, and dietary balance.

Yet another object of this invention is to provide certain novel manganese compounds wherein the manganese is not only in a form which can be readily absorbed and after ingestion readily distributed and utilized, but the manganese is associated in a complex form with an alpha amino acid, such as methionine, which also can be readily ingested and distributed in the body to provide adequate dietary levels of methionine for proper health, weight gain and dietary balance.

Yet another object of this invention is to provide a process for making novel manganese compounds which is simple to perform and can be economically utilized in large-scale plant practice to prepare the novel manganese compounds of this invention in bulk for ready utilization in large quantities to supplement the diets of animals and humans.

Still another object of this invention is to provide the compounds of this invention in a solid crystalline, water soluble form, which provides for compounds in an easily and efficiently useable form for supplementation of solid feeds.

The method of accomplishing these and other objects will become apparent from the following description of the invention.

DETAILED DESCRIPTION OF THE INVENTION

It is important to note that the manganese compounds of this invention are referred to herein as complexed salts. These salts are to be carefully distinguished from conventional salts such as, for example, manganese chloride. Conventional salts such as manganese chloride contain only an electrostatic attraction between the cation and the anion. The complexed salts of this invention differ from conventional salts in that while they have an electrostatic attraction between the cation and the anion, there is also a coordination bond between the manganese and the amino moiety of the amino acid, preferably methionine or glycine. The manganese alpha amino acid complexed salts have the formula:

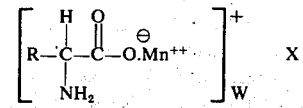

wherein R is an alpha moiety of alpha amino acid, preferably methionine or glycine, X is an anion, and W is an integer equal to the anion charge of X. The cation of these complexed salts is represented by the bracketed material in the above formula and represents a 1:1 complex of manganese and alpha amino acid. Sterically, the cation moiety can be represented as follows:

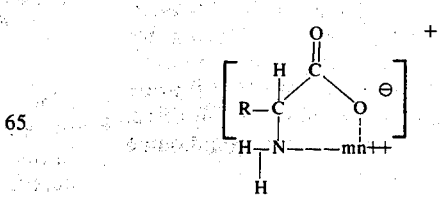

As can be seen from this formula, the five-membered ring formation exists when the manganese ion is complexed by coordinate bond with the amine moiety, and electrostatic attraction with the carboxylic acid moiety of the alpha amino acid. In addition, the complex is formed by a 1:1 ratio of an alpha amino acid molecule and a manganese ion with each manganese ion becoming complexed with only one alpha amino acid molecule. Providing 1:1 complex ions of the manganese and the alpha amino acid has been found of great importance in insuring gastro-intestinal absorption of the manganese and its subsequent distribution and effective utilization within the body biochemical system.

In the above described formula, X represents the anion. The selection of an anion is not critical but still of importance. The anion can be an inorganic anion, organic anion, a monovalent anion, a divalent anion, or a polyvalent anion. However, in order to have the molecules of the salt be electrostatically balanced, W is a whole number integer equal to the anionic charge of X.

Preferably, the source of the anion X is an inorganic acid or, if organic, from acetic acid. The most preferred anions are monovalent anions which are derived from acids which are readily commercially available, and which will not chemically react with the alpha amino acid to produce undesirable results. For example, the nitrate is not suitable because of its very high oxidation potentials with the result being that it often will oxidize the amino acid, particularly methionine, to produce undesirable side products. Halogens have likewise been found to be not suitable because the compounds of this invention apparently will not exist in a solid crystalline form when halogen anions are employed. Preferably the anion is acid sulphate, dihydrogen phosphate, or if organic, acetate.

If the anion is an organic anion moiety others than acetate can conceivably also be employed. For example, the anion could be derived from simple aliphatic carboxyllic acids, both monobasic carboxyllic acids and dibasic carboxyllic acids. For example, the anion can be propionate, or where the acid is a dibasic acid, succinate.

As heretofore explained, R is an alpha positioned moiety of an essential amino acid. Of course, essential alpha amino acids refer to those amino acids which must be fed to young animals and humans if proper growth is to take place. Apparently, these alpha amino acids which are deemed essential must be fed to the animals and humans, for that matter, as they evidently cannot be synthesized in large enough quantities by the animals from other materials in their diet. Those essential alpha amino acids which are preferred for utilization in forming the 1:1 complex salts of this invention are arginine, histidine, isoleucine, leucine, lysine, methionine, phenylalanine, threonine, tryptophane, and valine. Glycine, while not an essential amino acid, is also a preferred alpha amino acid in that it is readily available and can be utilized for synthesis of the complex salts of this invention. The two most preferred natural alpha amino acids are methionine and glycine. For glycine R represents hydrogen, and for methionine R represents the following:

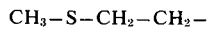

$CH_3-S-CH_2-CH_2-$

Surprisingly, a simple, straightforward and importantly economically feasible process of preparing these manganese methionine complexed salts in a form readily utilizable for dietary supplementation has been developed. From the standpoint of ease of production in solid crystalline form, it is preferred that the complexed salts of this invention be the acid sulphate salts. The acid sulphate salts are formed from manganese sulphate monohydrate which is readily commercially available. In addition, the acid sulphate complexed salts can be preferentially separated from the raction mixture by shifting the equilibrium of the reaction. As a result the process can be conveniently and efficiently operated.

The following examples are offered to further illustrate but not limit, the invention.

EXAMPLE 1

(Preparation of 1:1 manganese methionine acid sulphate)

dl-methionine (1.49 grams — .01 moles) was dissolved in about 70 milliliters of distilled water which was being warmed on a steam bath. The dissolved solution was then cooled. Manganese sulphate monohydrate (1.69 grams — .01 moles) was dissolved in about 15 milliliters of warm water and was then added to the previously described methionine solution.

The mixture was warmed on a steam bath and most of the water was removed over a rotary evaporator operating under high vacuum. Much of the water distilled at the bath temperature of between 48 and 55 degrees centigrade.

The residue obtained was dissolved in a minimum amount of hot water that would dissolve the residue and was thereafter filtered hot. To the filtrate was added absolute ethyl alcohol until turbidity was noted. It was then cooled in a freezer overnight.

A white granular residue of solid crystalline material was obtained. This was filtered and dried to provide a dry product weighing 2.2 grams. The melting point was determined and found to be between 244° and 254° centigrade. The sample was then dried over benzene (boiling under vacuum) overnight. The melting point was taken again and found to be 251° to 252° centigrade.

The sample was analyzed by infrared analysis, methionine analysis and quantitative analysis for carbon, hydrogen, nitrogen and manganese. Infrared analysis showed the absence of a strong peak at 2100 reciprocal centimeters, which is the characteristic peak for methionine. The different peak structures of the product from the peak structures of the reactants indicated the formation of 1:1 manganese methionine acid sulphate. Quantitative analysis showed the following:

| Theoretical Amount | Found Amount |
| --- | --- |
| 49.94% methionine | 51.78% methionine (average) |
| 18.3% manganese | 14.35% manganese (average) |
| 20.0% carbon | 21.7% carbon |
| 3.69% hydrogen | 4.63% hydrogen |
| 4.66% nitrogen | 4.71% nitrogen |

The close parallel between the quantitative analysis theoretical amounts and actual found amounts, the infrared analysis, and the differing melting point characteristics, all indicated the presence of desired compound.

The resulting 1:1 manganese methionine acid sulphate is a white crystalline material. It is readily soluble in water at ratio of 1 gram in 5 milliliters of water at 15° Centigrade and the solution was stable on standing. The product is readily soluble in both simulated gastric juice and simulated intestinal juice. These solubility characteristics are to be contrasted with the slow dissolution of either manganese sulphate or methionine under similar conditions in water.

EXAMPLE 2

(1:1 manganese glycine acid sulphate)

A small sample of glycine was dried under high vacuum over boiling benzene. The sample was cooled and its melting point revealed that the sample was glycine (290° centigrade). 1.5 grams (0.02 moles) of the glycine was dissolved in 10 milliliters of distilled water. Manganese sulphate monohydrate, 3.3 grams, (0.02 moles) was dissolved in 25 milliliters of water while warming the solution. Both solutions were mixed together and stirred on the steam bath for about 1 hour and thereafter filtered while hot. The filtrate was cooled, absolute ethyl alcohol was added to it until it turned turbid. The turbid layer separated at the bottom of the beaker and was immiscible with the alcohol. The beaker was then left at room temperature overnight.

In the morning the liquid layer had turned into a thick, hard solid cake of crystalline material. It was separated, powdered and fresh absolute ethyl alcohol was added to it to dissolve the solid material. The whole thing was filtered and the residue was dried under high vacuum. Instrumental infrared analysis, quantitative analysis, and melting point analysis, as described previously, was conducted.

The infrared analysis showed an entirely different spectrum along the fingerprint region for glycine indicating the formation of a different compound. In addition, melting point analysis showed the compound did not melt up to 350° centigrade. Since glycine melts at 290° centigrade and manganese sulphate melts at 252° centigrade, the formation of a different compound was indicated.

Quantitative analysis showed a theoretical amount of manganese of 24.3% in 1:1 manganese glycine acid sulphate, and an actual measured amount of 24.28%. A theoretical amount of glycine at 33.0%, and an actual found amount of 27.0%. A theoretical amount of hydrogren of 2.3% and an actual found amount of 2.2%. Finally, a theoretically found amount of nitrogen at 6.19% and an actual found amount at 5.88%. These values closely correspond to the theoretical values and indicate further the formation of desired compound.

What is claimed is:

1. 1.1 manganese glycine complexed salts of the formula:

$$[H_2C(H_2N)COO.Mn^{++}]_W{}^+X$$

wherein X is an anion selected from the group consisting of sulphates, phosphates and acetate and W is an integer equal to the anionic charge of X.

2. The compound of claim 1 wherein X is acid sulphate.

3. In solid form a water soluble 1 . 1 manganese methionine complexed salts of the formula:

$$[CH_3SCH_2CH_2CH(NH_2)COO \cdot Mn^{++}]_W{}^+X$$

wherein X is an anion selected from the group consisting of sulphates, phosphates and acetate and W is an integer equal to the anionic charge of X.

4. The compound of claim 3 wherein X is acid sulphate.

5. A process of making solid form 1:1 manganese methionine acid sulphate, comprising:
   reacting substantially equimolar quantities of water dissolved methionine and water dissolved manganese sulphate to provide a reaction product,
   separating the reaction product,
   dissolving the reaction product in a minimum amount of hot water needed to dissolve said reaction product, and
   adding ethyl alcohol to reprecipitate the desired product in solid form.

* * * * *